(12) United States Patent
Burnett

(10) Patent No.: US 8,771,221 B2
(45) Date of Patent: *Jul. 8, 2014

(54) IMPLANTABLE FLUID MANAGEMENT DEVICE FOR THE REMOVAL OF EXCESS FLUID

(71) Applicant: Sequana Medical AG, Zug (CH)

(72) Inventor: Daniel R. Burnett, San Francisco, CA (US)

(73) Assignee: Sequana Medical AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/789,250

(22) Filed: Mar. 7, 2013

(65) Prior Publication Data

US 2013/0253409 A1    Sep. 26, 2013

Related U.S. Application Data

(63) Continuation of application No. 11/933,214, filed on Oct. 31, 2007, now Pat. No. 8,398,577, which is a continuation-in-part of application No. 10/826,237, filed on Apr. 17, 2004, now Pat. No. 7,909,790, which is a continuation of application No. 10/700,863, filed on Nov. 3, 2003, now Pat. No. 7,311,690.

(60) Provisional application No. 60/855,247, filed on Oct. 31, 2006.

(51) Int. Cl.
*A61M 27/00* (2006.01)
*A61M 31/00* (2006.01)

(52) U.S. Cl.
CPC .............. *A61M 27/002* (2013.01); *A61M 31/00* (2013.01); *A61M 2210/1085* (2013.01); *A61M 2202/0014* (2013.01); *A61M 2202/0401* (2013.01); *A61M 2205/04* (2013.01); *A61M 2205/10* (2013.01); *A61M 2205/3331* (2013.01); *A61M 2210/1017* (2013.01)
USPC ..................... 604/9; 604/8; 604/10; 604/540

(58) Field of Classification Search
CPC ... A61M 27/002; A61M 29/00; A61M 31/00; A61M 2027/002; A61M 2202/0014; A61M 2202/0401; A61M 2202/0496; A61M 2205/04; A61M 2205/10; A61M 2205/3331; A61M 2205/3334; A61M 2205/3337; A61M 2205/3341; A61M 2205/3344
USPC ........ 604/9, 48, 503, 506, 65, 73, 93.01, 118, 604/131, 156, 264, 540; 623/23.64, 23.74, 623/23.76, 26
See application file for complete search history.

(56) References Cited

U.S. PATENT DOCUMENTS

| 3,233,610 A | 2/1966 | Stanley |
| 3,516,410 A | 6/1970 | Salomon |

(Continued)

FOREIGN PATENT DOCUMENTS

| GB | 2 350 794 | 12/2000 |
| JP | 63-143074 | 6/1988 |

(Continued)

OTHER PUBLICATIONS

Costanzo et al., "Early Ultrafiltration in Patients with Decompensated Heart Failure and Diuretic Resistance," J. Am. Coll. Cardiol., (2005), 46(11):2047-2051.

(Continued)

*Primary Examiner* — Adam Marcetich
(74) *Attorney, Agent, or Firm* — Foley & Lardner LLP; Christopher C. Bolten; Nicola A. Pisano

(57) ABSTRACT

A device for removing fluid from a first bodily cavity and for directing that fluid into a second bodily cavity while avoiding risks of infection and, in one embodiment, excessive dehydration of the first bodily cavity. The device includes an uptake tube having a proximal end in fluid communication with the first bodily cavity and a distal end in fluid communication with a pump, and an outflow tube having a proximal end in fluid communication with the pump and a distal end in fluid communication with the second bodily cavity. The distal end of the uptake tube may be coupled to a reservoir configured to expand upon ingression of fluid into the reservoir and to contract upon removal of fluid due to a negative pressure provided by the pump.

20 Claims, 16 Drawing Sheets

(56) References Cited

U.S. PATENT DOCUMENTS

| | | |
|---|---|---|
| 3,540,451 A | 11/1970 | Zeman |
| 3,575,158 A | 4/1971 | Summers |
| 3,608,088 A | 9/1971 | Dorman et al. |
| 3,626,950 A | 12/1971 | Schulte |
| 3,654,932 A | 4/1972 | Newkirk et al. |
| 3,669,116 A | 6/1972 | Heyer |
| 3,810,259 A | 5/1974 | Summers |
| 3,910,283 A | 10/1975 | Leveen |
| 4,083,786 A | 4/1978 | Tsuda et al. |
| 4,240,434 A | 12/1980 | Newkirk |
| 4,261,341 A | 4/1981 | Hakim et al. |
| 4,368,737 A | 1/1983 | Ash |
| 4,416,657 A | 11/1983 | Berglund |
| 4,468,219 A | 8/1984 | George et al. |
| 4,557,724 A | 12/1985 | Gregonis et al. |
| 4,584,994 A | 4/1986 | Bamberger et al. |
| 4,595,390 A | 6/1986 | Hakim et al. |
| 4,610,625 A | 9/1986 | Bunn |
| 4,610,658 A | 9/1986 | Buchwald et al. |
| 4,615,691 A | 10/1986 | Hakim et al. |
| 4,618,343 A | 10/1986 | Polaschegg |
| 4,657,530 A | 4/1987 | Buchwald et al. |
| 4,690,673 A | 9/1987 | Bloomquist |
| 4,725,207 A | 2/1988 | Buchwald et al. |
| 4,779,614 A | 10/1988 | Moise |
| 4,850,955 A | 7/1989 | Newkirk |
| 4,904,236 A | 2/1990 | Redmond et al. |
| 4,950,232 A | 8/1990 | Ruzicka et al. |
| 4,963,129 A | 10/1990 | Rusch |
| 5,021,048 A | 6/1991 | Buckholtz |
| 5,037,385 A * | 8/1991 | O'Byrne ............... 604/28 |
| 5,045,057 A | 9/1991 | Van Driessche et al. |
| 5,071,408 A | 12/1991 | Ahmed |
| 5,078,688 A | 1/1992 | Lobodzinski et al. |
| 5,141,493 A | 8/1992 | Jacobsen et al. |
| 5,147,281 A | 9/1992 | Thornton et al. |
| 5,167,615 A | 12/1992 | East et al. |
| 5,254,084 A | 10/1993 | Geary |
| 5,356,386 A | 10/1994 | Goldberg et al. |
| 5,360,414 A | 11/1994 | Yarger |
| 5,385,541 A | 1/1995 | Kirsch et al. |
| 5,387,188 A | 2/1995 | Watson |
| 5,391,143 A | 2/1995 | Kensey |
| 5,395,320 A | 3/1995 | Padda et al. |
| 5,395,350 A | 3/1995 | Summers |
| 5,397,354 A | 3/1995 | Wilk et al. |
| 5,431,637 A | 7/1995 | Okada et al. |
| 5,472,323 A | 12/1995 | Hirabayashi et al. |
| 5,474,683 A | 12/1995 | Bryant et al. |
| 5,489,276 A | 2/1996 | Jamshidi |
| 5,520,632 A | 5/1996 | Leveen et al. |
| 5,575,770 A | 11/1996 | Melsky et al. |
| 5,637,083 A | 6/1997 | Bertrand et al. |
| 5,725,506 A | 3/1998 | Freeman et al. |
| 5,830,172 A | 11/1998 | Leveen et al. |
| 5,902,336 A | 5/1999 | Mishkin |
| 5,947,911 A | 9/1999 | Wong et al. |
| 5,980,478 A | 11/1999 | Gorsuch et al. |
| 5,989,207 A | 11/1999 | Hughes |
| 6,007,511 A | 12/1999 | Prywes |
| 6,017,355 A | 1/2000 | Hessel et al. |
| D420,738 S | 2/2000 | Carter et al. |
| 6,022,333 A | 2/2000 | Kensey |
| 6,132,415 A | 10/2000 | Finch et al. |
| 6,162,238 A | 12/2000 | Kaplan et al. |
| 6,162,487 A | 12/2000 | Darouiche |
| 6,193,684 B1 | 2/2001 | Burbank et al. |
| 6,254,567 B1 | 7/2001 | Treu et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,533,733 B1 | 3/2003 | Ericson et al. |
| 6,689,085 B1 | 2/2004 | Rubenstein et al. |
| 6,827,682 B2 | 12/2004 | Bugge et al. |
| 6,846,168 B2 | 1/2005 | Davis et al. |
| 6,875,192 B1 | 4/2005 | Saul et al. |
| 6,887,214 B1 | 5/2005 | Levin et al. |
| 6,894,456 B2 | 5/2005 | Tsukamoto et al. |
| 6,905,474 B2 | 6/2005 | Borgesen |
| 6,926,691 B2 | 8/2005 | Miethke |
| 6,955,655 B2 | 10/2005 | Burbank et al. |
| 7,025,739 B2 | 4/2006 | Saul |
| 7,025,742 B2 | 4/2006 | Rubenstein et al. |
| 7,128,735 B2 | 10/2006 | Weston |
| 7,195,608 B2 | 3/2007 | Burnett |
| 7,311,690 B2 | 12/2007 | Burnett |
| 7,335,179 B2 | 2/2008 | Burnett |
| 7,419,483 B2 | 9/2008 | Shehada |
| 7,909,790 B2 | 3/2011 | Burnett |
| 2001/0025170 A1 | 9/2001 | Paderni |
| 2001/0027289 A1 | 10/2001 | Treu et al. |
| 2002/0013545 A1 | 1/2002 | Soltanpour et al. |
| 2002/0022793 A1 | 2/2002 | Bertrand et al. |
| 2003/0163079 A1 | 8/2003 | Burnett |
| 2003/0217962 A1 | 11/2003 | Childers et al. |
| 2004/0049288 A1 | 3/2004 | Levin |
| 2004/0106205 A1 | 6/2004 | Stevenson et al. |
| 2004/0147871 A1 | 7/2004 | Burnett |
| 2005/0096582 A1 | 5/2005 | Burnett |
| 2005/0131340 A1 | 6/2005 | Sorenson et al. |
| 2005/0273034 A1 | 12/2005 | Burnett |
| 2006/0036208 A1 | 2/2006 | Burnett |
| 2006/0058731 A1 | 3/2006 | Burnett et al. |
| 2007/0106205 A1 | 5/2007 | Connell et al. |
| 2008/0108935 A1 | 5/2008 | Nyhart, Jr. |
| 2008/0154173 A1 | 6/2008 | Burnett |

FOREIGN PATENT DOCUMENTS

| | | |
|---|---|---|
| JP | 52-070786 | 10/1993 |
| JP | 09-056810 | 3/1997 |
| JP | 2006-507018 | 2/2006 |
| WO | WO-97/41799 | 11/1997 |
| WO | WO-98/16171 | 4/1998 |
| WO | WO-03/072166 | 9/2003 |

OTHER PUBLICATIONS

Geitz et al., "Pulsatile brain movement and associated hydrodynamics studied by magnetic resonance phase imaging," Diagnostic Neuroradiolgy, (1992), 34(5):370-380.

Houlberg et al., "Terminal Right Heart Failure Due to Complex Congenital Cardiac Disease Successfully Managed by Home Peritoneal Drainage," Cardiol. Young., (2003), 13:568-570.

International Search Report dated Jul. 17, 2003 in related International PCT Appl. No. PCT/US03/05145.

Ortiz et al., "Long-term Automated Peritoneal Dialysis in Patients with Refractory Congestive Heart Failure," Advances in Peritoneal Dialysis, (2003), 19:77-80.

Rozenblit, "Peritoneal-Urinary Drainage for Treatment of Refractory Ascites: A Pilot Study," NY Journal of Vascular & Interventional Radiology, (Nov./Dec. 1998) 9(6):998-1005.

\* cited by examiner

IMPLANTABLE FLUID MANAGEMENT DEVICE FOR THE REMOVAL OF EXCESS FLUID

CROSS-REFERENCE TO RELATED PATENT APPLICATIONS

This application is a continuation of U.S. patent application Ser. No. 11/933,214, filed Oct. 31, 2007, now U.S. Pat. No. 8,398,577, which is a continuation-in-part of U.S. patent application Ser. No. 10/826,237, filed Apr. 27, 2004, now U.S. Pat. No. 7,909,790, which is a continuation application of U.S. patent application Ser. No. 10/700,863, filed Nov. 3, 2003, now U.S. Pat. No. 7,311,690. U.S. patent application Ser. No. 11/933,214 also claims the benefit of the priority of U.S. Provisional Patent Application Ser. No. 60/855,247, filed on Oct. 31, 2006, the entirety of which is incorporated herein by reference.

FIELD OF THE INVENTION

The present invention relates to a medical device for removing excessive bodily fluids during the treatment of ailments related to chronic fluid collections, for example, congestive heart failures. More particularly, the present invention relates to a pump-assisted transvesicular drainage device for transferring excessive fluid from a first body cavity to a second body cavity.

BACKGROUND OF THE INVENTION

Various medical conditions result in pathologic collections of bodily fluids. One such conditions is congestive heart failure (CHF), which causes the heart to be unable to effectively meet the oxygen needs of other organs. CHF usually occurs in adults after an injury to the heart, for example, after myocardial infarction, which causes the pumping action of the heart to be ineffective. CHF may also occur in the presence of a near-normal cardiac function under conditions of hi) 11 demand, for example, because of an increase of blood volume due to retention of salt and water or because of tachycardia. These compensatory changes burden the cardiac function, leading to progressive CHF.

In terms of incidence, prevalence, morbidity, and mortality, the epidemiologic magnitude of CHF is staggering. In the United States, the estimated annual cost of heart failure is $60 billion. Approximately one million U.S. hospital admissions per year are attributable to a primary diagnosis of acutely decompensated heart failure and the estimated annual cost of inpatient care for CHF patients is $23 billion.

Until recently, the only therapies for delaying progress of this illness were diuretics and heart-assist devices. Fluid accumulation related to CHF is typically treated by diuretics in the early stages of the condition, but over time the body builds resistance to diuretics and the patient then begins to retain fluid. Fluid and salt restrictions may be imposed, but despite these measures, most patients continue to accumulate fluid with cardiac function deteriorating over time, which results in further fluid accumulation until the patient receives a heart transplant or succumbs to his illness.

In three recent publications, the use of peritoneal dialysis was explored in the treatment of refractory CHF: COSTANZO ET AL., Early Ultrafiltration in Patients with Decompensated Heart Failure and Diuretic Resistance, J. Am. Coll. Cardiol. 2005; 46: 2047-2051, HOULBERG ET AL., Terminal right heart failure due to complex congenital cardiac disease successfully managed by home peritoneal drainage, Cardiol. Young 2003; 13: 568-570, and ORTIZ ET AL., Long-term automated peritoneal dialysis in patients with refractory congestive heart failure, Advances in Peritoneal Dialysis, 2003; 19; 77-80. In each of these publications, the patients were subjected to standard peritoneal dialysis and their conditions stabilized or even improved. This treatment requires the patients to undergo peritoneal dialysis exchanges, with the use of an external catheter and great risk of infection.

Various devices have been disclosed in the prior art for removing excess fluid from different body organs, for example, in U.S. Pat. No. 4,610,658 to Buchwald et al.; U.S. Pat. No. 4,850,955 to Newkirk; U.S. Pat. No. 6,132,415 to Finch et al.; U.S. Pat. No. 6,264,625 to Rubenstein et al.; and in U.S. Patent Application Publication 2005/0273034 to Burnett. The devices of the prior art, however, exhibit different shortcomings, for example, provide no system for preventing an excessive removal of fluids from a bodily cavity, or for preventing accumulation of tissue ingrowth into an implanted fluid collection system, which would cause the system to fail to operate properly over time.

SUMMARY OF THE INVENTION

The present invention relates to a device and its method of use for periodically, or on an as needed basis, removing fluid from a first bodily cavity, for example, from the peritoneal cavity or the lungs, and for transferring that fluid to a second bodily cavity, for example, the bladder. By the use of a device constructed according to the principles of the present invention, risk of infection is avoided fluid removal may be limited to the extent necessary to treat a specific aliment without unnecessarily dehydrating the cavity producing the excessive fluid. Therefore, the present invention provides the benefits but avoids the drawbacks of peritoneal dialysis to treat CHF and other pathological conditions, and also provides an improvement over devices of the prior art that cause excess fluid removal from a target bodily cavity.

In one embodiment, an implantable fluid management device according to the present invention includes an uptake tube having a proximal end in fluid communication with a first cavity in the body of a patient and a distal end in fluid communication with a pump, and further includes an outflow tube having a proximal end in fluid communication with the pump and a distal end in fluid communication with a second cavity in the body of the patient. The distal end of the uptake tube is coupled to a reservoir that is configured to expand upon ingression of fluid into the reservoir and to contract upon removal of the fluid caused by a negative pressure applied on the reservoir by the pump.

The reservoir has an outer surface with perforations that provide fluid communication between the first cavity and the reservoir, and may be manufactured with different shapes, for example, hemispherical or cylindrical. The uptake tube may be coupled to the reservoir in different point, for example, centrally or laterally.

The reservoir may be supported by a support structure, which may provide a basic frame to the reservoir or may be made from a material that causes the support structure of the reservoir to recoil after contracting and to reacquire its expanded configuration. Therefore, the reservoir may be refilled and expand gently due to ingression of the fluid from the cavity, or expansion may be promoted by a recoil of the support structure. Backflow from the outflow tube to the uptake tube may be prevented with different unidirectional systems, for example, by adding a unidirectional valve to the device or by employing a unidirectional pump.

The reservoir may also include a plurality of recesses on a portion of its outer surface, which promote flow of the fluid towards at least some of the perforations. The surface spanning between those recesses may be made or coated with a material favoring tissue ingrowth within that surface, so to anchor the reservoir to the cavity. Moreover, to prevent clogging of the perforations, or a blockage of the perforation by contact with a wall of the bodily cavity, at least some of the perforations may be disposed in recessed positions in relation to the outer surface of the reservoir.

A dehydration prevention element may be included in the reservoir for preventing an actuation of the pump when the reservoir is in the contracted condition, so to avoid an excess removal of fluid from the bodily cavity by forcing a flow of fluid from the cavity into the reservoir. A weight may also be disposed in the reservoir to force the reservoir to acquire a desired position within the cavity after implantation of the device.

In one embodiment, the perforations on the surface of the reservoir may be semi-permeable, in order to prevent ingression into the reservoir and to filter out certain undesirable components of the fluid.

In one embodiment, the device includes a reservoir formed by a first reservoir element and a second reservoir element in fluid communication one with the other. Each of the first and second reservoir elements is configured to hold fluid and to contract upon actuation of the pump. An annular surface couples the first element to the second element and is configured like a groove defined by a portion of the first element and by a portion of the second element. Openings in the annular surface enable ingression of the fluid into the reservoir.

In one embodiment, the first and second elements are each shaped like expandable disks having circumferential perimeters one parallel to the other, and the annular surface is disposed parallel to the first and second elements. Recesses are disposed radially on the outer face of the annular surface, promoting flow of the fluid to the openings in the annular surface. Those recesses also define ribs along the inner face of the annular surface, stiffening a portion of the reservoir and favoring expansion and contraction of the reservoir along predetermined directions.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

The present invention concerns a device and a related method for removing fluid from a body cavity. An excessive drainage of fluid may be prevented by coupling an uptake tube to a reservoir constructed as described hereinbelow.

Figure 1:
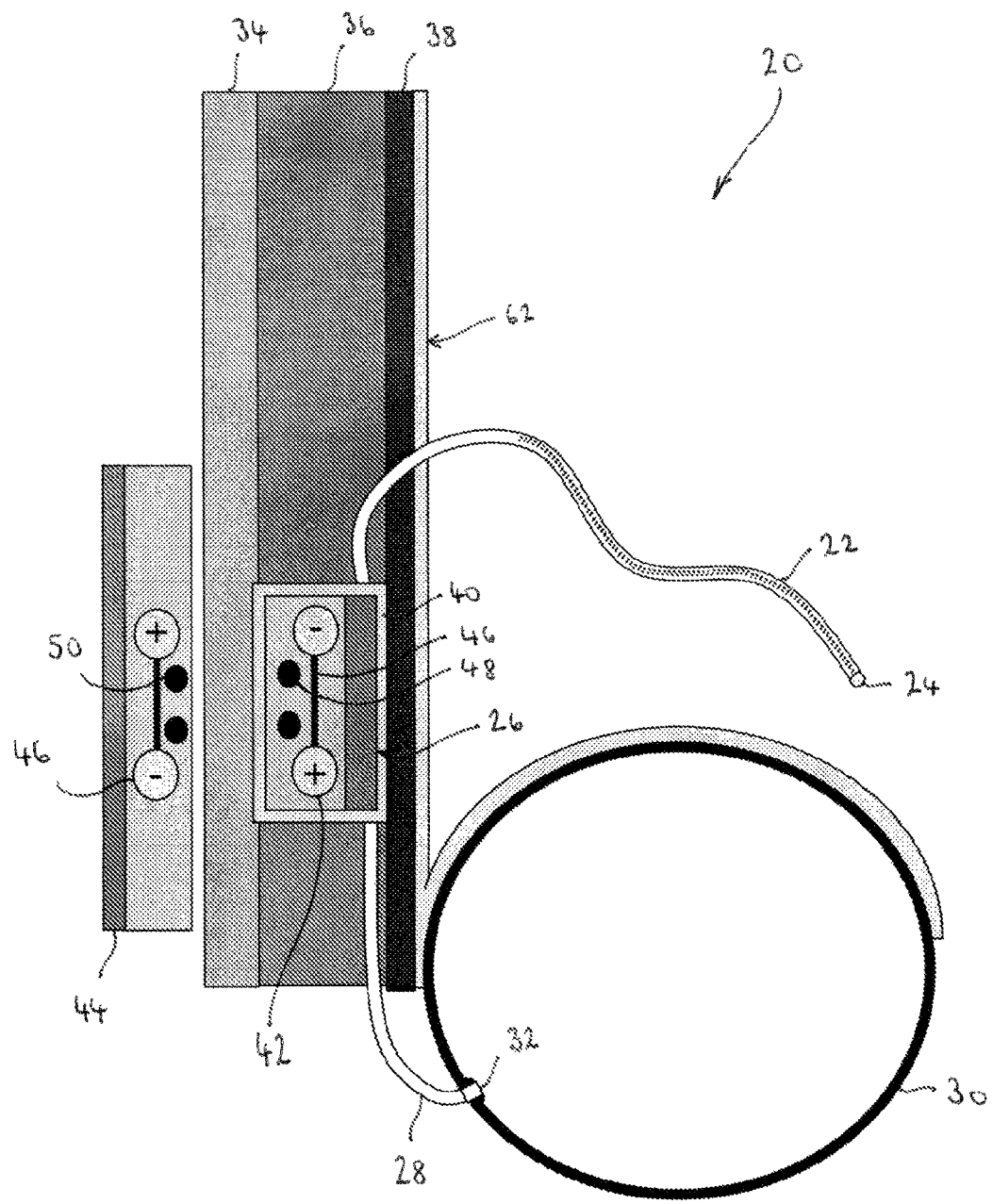
FIG. 1 illustrates an embodiment of the invention, in which an implanted draining device is magnetically coupled to an external drive.

FIG. 1 illustrates a first embodiment of a device 20 from removing excess fluid from a body region. Device 20 may be utilized, for example, to remove excess fluid from the space between the lungs and the chest wall. Fluid accumulated in this area, called the pleural space, may lead to various diseases or disorders, such as CHF, lung infection, kidney disease, pulmonary embolism, cancer, and cirrhosis of the liver. The most severe expression of CHF, pulmonary edema, causes lung fluid to increase due to a leakage from pulmonary capillaries into the interstitium and alveoli of the lungs due to the inability of the left ventricle to effectively pump blood out.

In the embodiment depicted in FIG. 1, excess fluid is taken up and carried away from a body region by uptake tube 22, which may have a solid wall or a wall that is at least partially perforated to prevent blockage. Alternate embodiments of the invention include an uptake screen at proximal end 24 of uptake tube 22. Uptake tube 22 is generally composed of a conduit for fluid transport, such as but not limited to, a catheter, a channel, a lumen within a device, a hose, a pipe, a duct, an artery or a vessel.

Uptake tube 22 leads the fluid to the pump 26, which transfers the fluid from uptake tube 22 to an outflow tube 28 and into a second body region, for example, into the bladder 28. In a preferred variant of this embodiment, outflow tube 28 is coupled to bladder 30 with a bladder anchor 32, which secures outflow tube 28 to bladder 30 and prevents detachment during bladder contraction. Bladder anchor 32 may be secured to bladder 30 in different ways, for example, with a simple pigtail catheter element, one or more flanges, a screw thread on an outer surface of anchor 32, staples, sutures, an adhesive compound, a porous solid promoting interstitial cell growth, and/or one or more barbs.

Pump 26 may be powered and operated by electromechanical forces or preferably by magnetic coupling and is placed under skin 34 either in a subcutaneous space 36 or in the musculature of abdominal wall 38. Pump 36 is preferably a peristaltic pump, but may also be a gear pump, turbine pump, impeller pump, radial flow pump, centrifugal pump, piston pump, or any other pump type. Pump 26 is preferably enclosed in a housing, shroud or casing 40 made of a biocompatible material and is preferably configured to ensure unidirectional operation, and, in one variant of the present embodiment, valves (not shown) may also be included to ensure unidirectional operation from uptake tube 22 to outflow tune 28.

Housing 40 encloses a magnetically coupled drive, which contains one or more magnets 42 for operating pump 26. A control module 44 drives one or more external magnets 46 or electromagnetic fields, thus providing a magnetic field to implanted magnets 42. By rotating magnets 46 within control module 44, magnets 42 are caused to move, transferring their kinetic force through drive 46 and actuating pump 26. While FIG. 1 shows control module 44 as having a motor and a linkage, any magnetically powered system that causes pump magnets 42 to rotate could be used to operate pump 26. Alternatively, pump 26 may be electromechanically powered through an implanted battery (not shown) actuated and monitored externally, without the use of magnetic coupling. Sensors 48 and 50 are built into the interfaces of control unit 44 and implanted pump 26, enabling a user to ensure that pump 26 and drive 46 are engaged and able to transfer power. These sensors 48 and 50 also transfer information from pump 26 to the drive 44 during operation to monitor pressures and/or flow and/or other parameters of interest. Magnets may also be employed to anchor pump 26 by opposing against rotational forces generated during operation of pump 26.

Figure 2A:
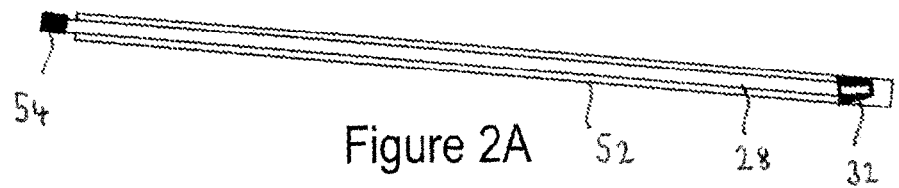
FIGS. 2A-2C illustrate detail components of the embodiment of FIG. 1, more particularly, an outflow tube prior to implanting (FIG. 2A), an uptake tube prior to implanting (FIG. 2B), and a pump (FIG. 2C).
Figure 2B:
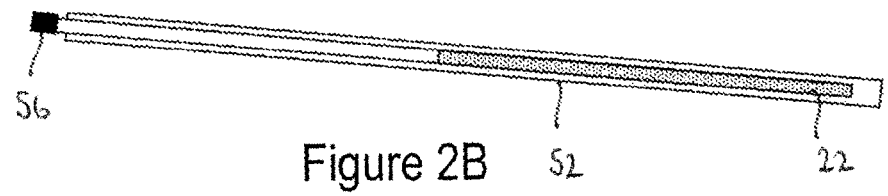
Figure 2C:
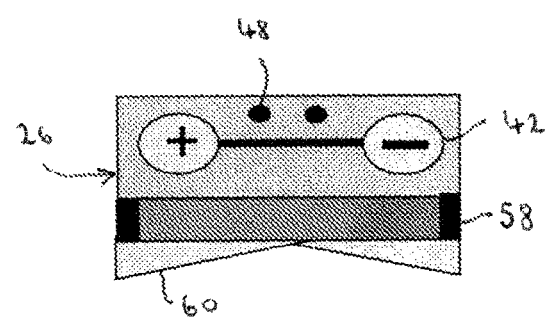

Certain components of device 20 are shown in detail in FIGS. 2A-2C. More specifically, FIG. 2A illustrates outflow tube 28 disposed in its insertion trocar 52, as well as bladder anchor 32 and removably attachable port 54, preferably designed to interact with insertion port 56 on pump 26 after tube implantation. FIG. 2B illustrates inflow drainage tube 22 in its insertion trocar 17 with its removably attachable port 56. FIG. 2C illustrates implantable pump 26 with tubing detached. Pump 26 is illustrated as having anchors 58 for resisting rotational forces generated during pump use. For example, pump housing 40 may be anchored to a wall of the bodily cavity by barbed insertion pins 58 and/or materials designed to promote fibrotic ingrowth, so that pump 26 becomes anchored within muscle 38 or subcutaneous space 36 of abdominal wall 62. Alternative variants of device 20 include other anchoring mechanisms, for example, a screw thread on the outside of housing 40, staples, sutures, an adhesive compound, a porous solid promoting interstitial cell growth, and/or one or more pins designed to be inserted into subcutaneous space 36 and/or muscle 38 of abdominal wall 62.

Alternative embodiments of pump 26 include designs in which tubes 22 and 28 are permanently attached to pump 26 during manufacture and cannot be placed independently. In one embodiment, the components are provided separate and placed individually, such that tubes 22 and 28 are first inserted through a single incision into the body of the patient, then pump 26 is attached to both tubes 22 and 28 and securely placed in the implantation site.

Figure 3:
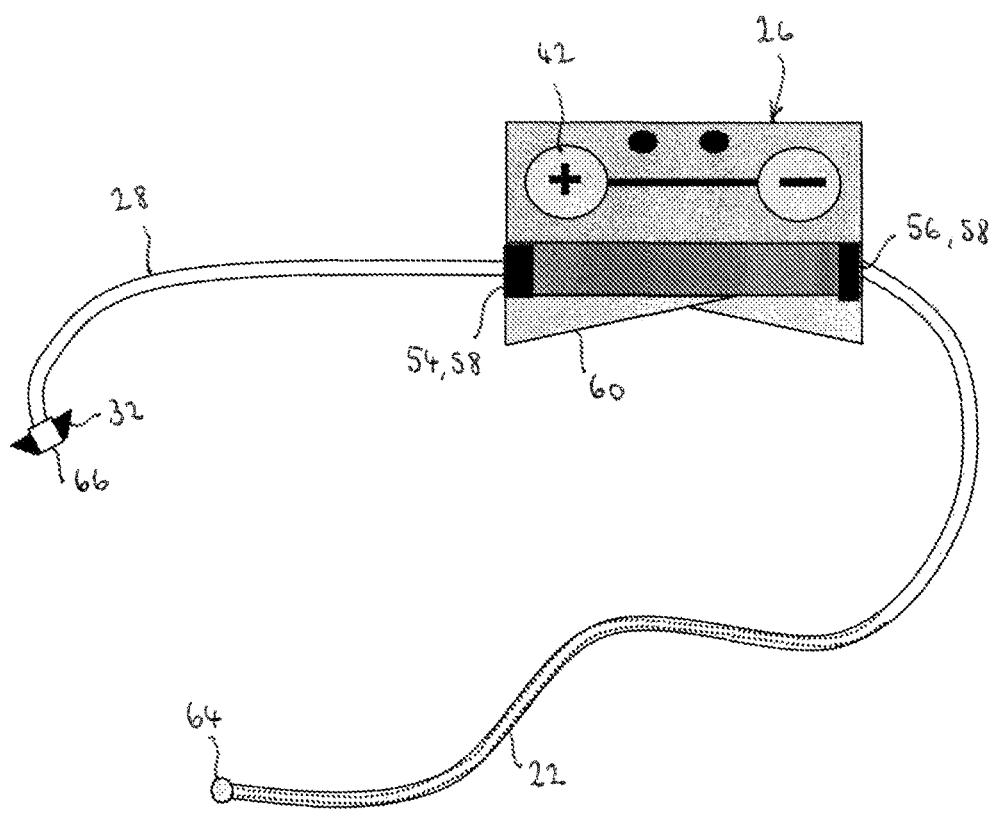
FIG. 3 illustrates an embodiment of the invention, in which a pump is attached to uptake and outflow tubes and includes an anchoring system.

FIG. 3 illustrates pump 26 and tubes 22 and 28 of FIG. 2, with tubes 22 and 28 attached to pump 26 at the ports 54 and 56 of pump 26. Also shown are optional pressure/chemical sensors 64 and 66 at the proximal end of uptake tube 22 and at the distal end of outflow tube 28. These sensors 64 and 66 provide positive and negative feedback to control mechanism 44 for controlling fluid flows.

Figure 4:
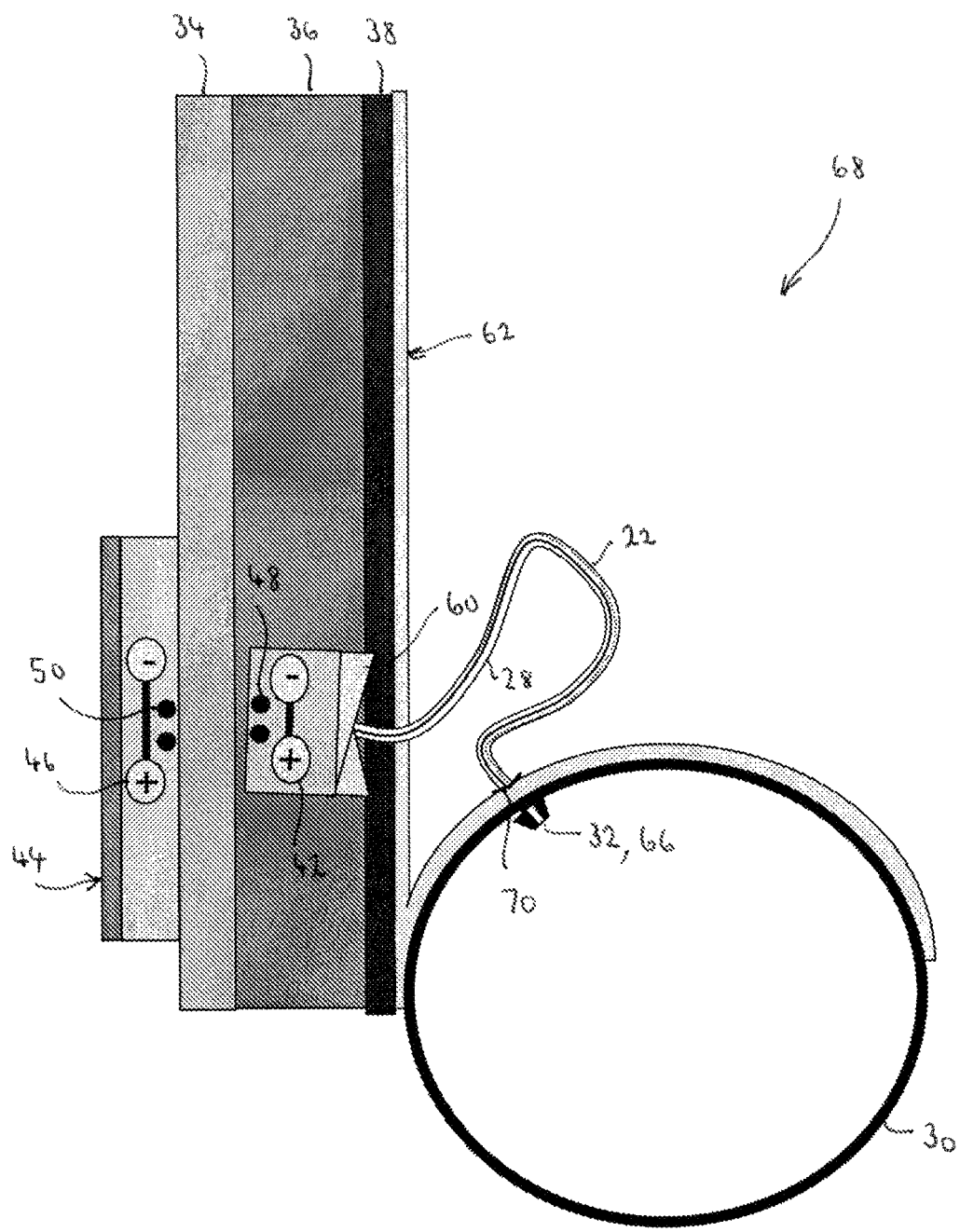
FIG. 4 illustrates an embodiment of the invention, in which the uptake and outflow tubes are adjacent one to the other.

FIG. 4 illustrates another embodiment of the invention, in which a device 68 has uptake and outflow tubes 22 and 28 disposed within a common tube. This configuration is particularly suited for body regions sharing a common wall, for example, the peritoneal cavity and bladder 30, making the insertion of a single dual-lumen tube a possibility. Also shown is the over-insertion prevention flange 70, which can be utilized to prevent insertion of uptake tube 22 into bladder 10 in the event of the single-puncture placement.

Figure 5:
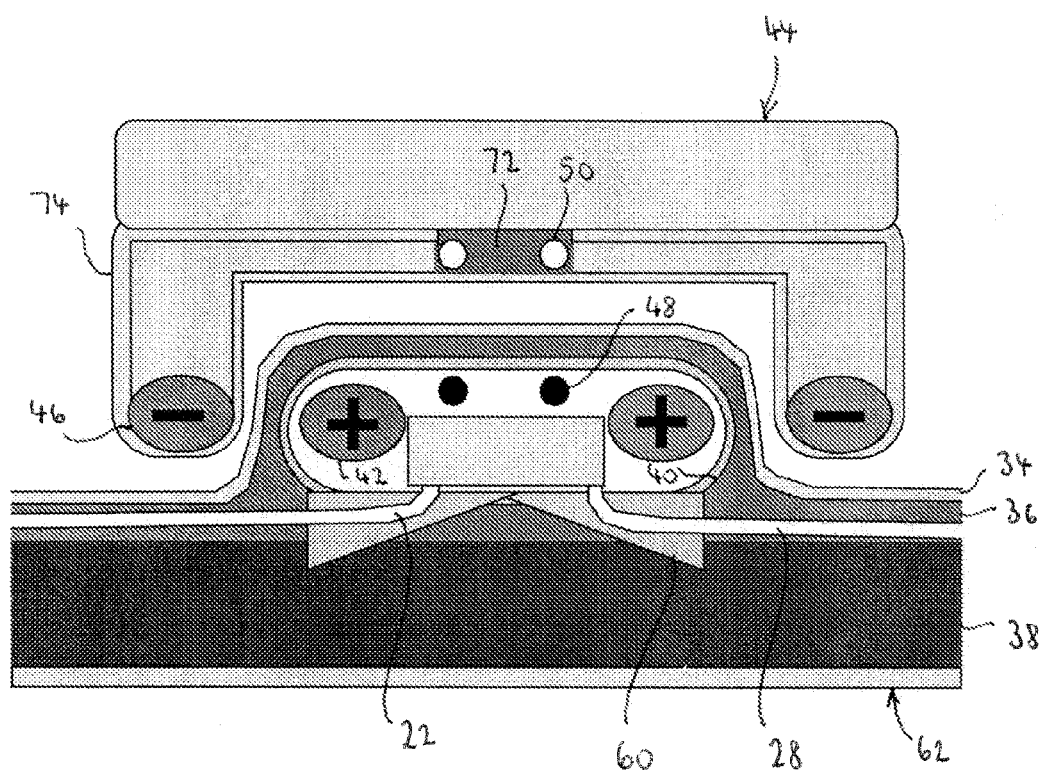
FIG. 5 illustrates a magnetically-coupled embodiment of the pump and external interface, in which the magnetic interaction between the pump and the external interface is circumferential.

FIG. 5 illustrates an embodiment of the invention, in which the magnetic coupling mechanism employed in the device for removing excess fluid enables a circumferential interaction. Pump magnets 42 sit inside the inner diameter of, and in the same plane as, external drive magnets 46, thereby preventing excess pressure on skin 34 over the site of insertion. In FIG. 5, drive shaft 72 is shown, which transfers power to magnet holding arm 74 of the drive. This design can also employ anchors 60, sensors 48, 50 and other features of the pump and tubing that were described hereinabove.

Figure 6:
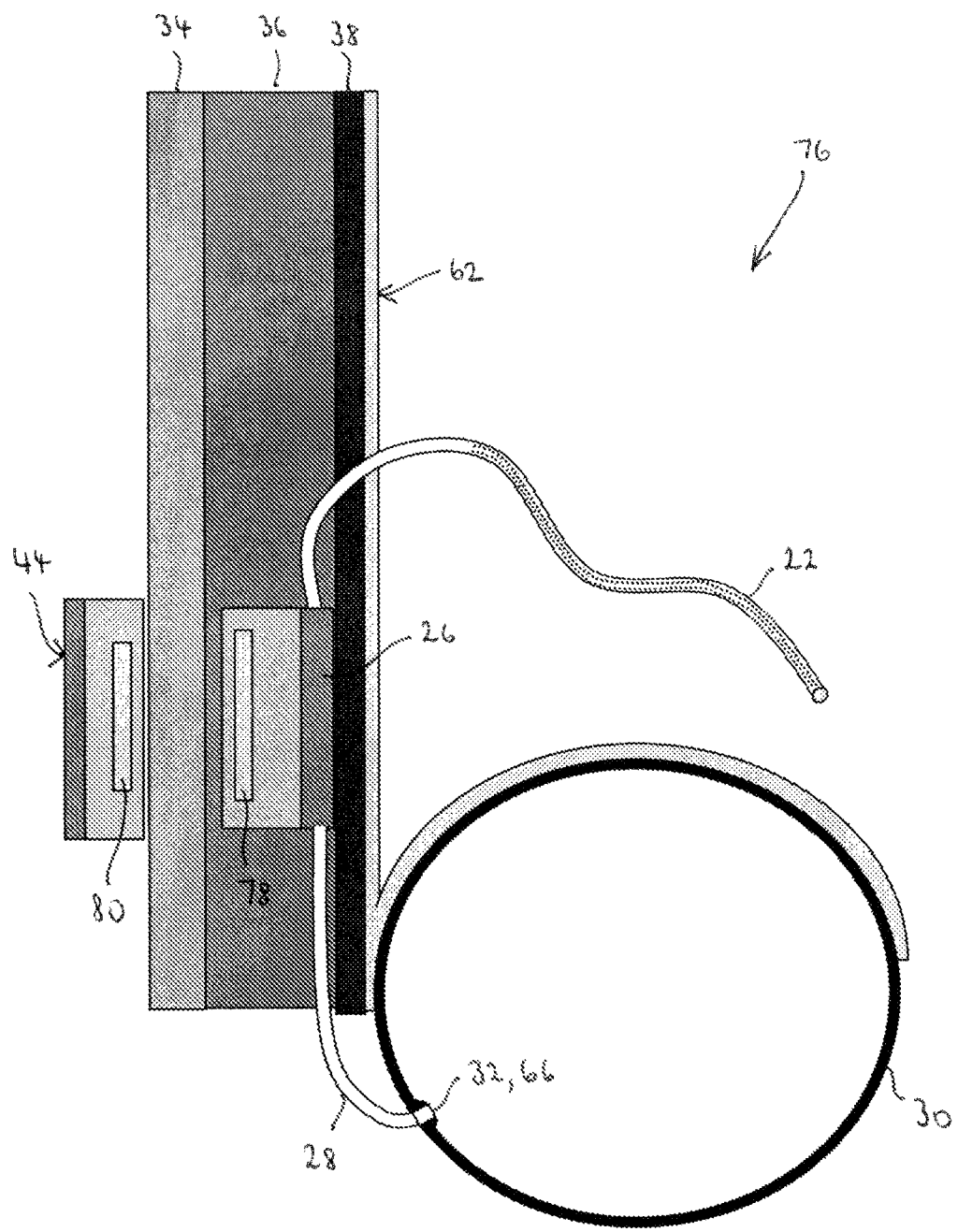
FIG. 6 illustrates an embodiment of the invention, in which the implanted pump is rechargeable but it not directly powered by the external interface.
Figure 7:
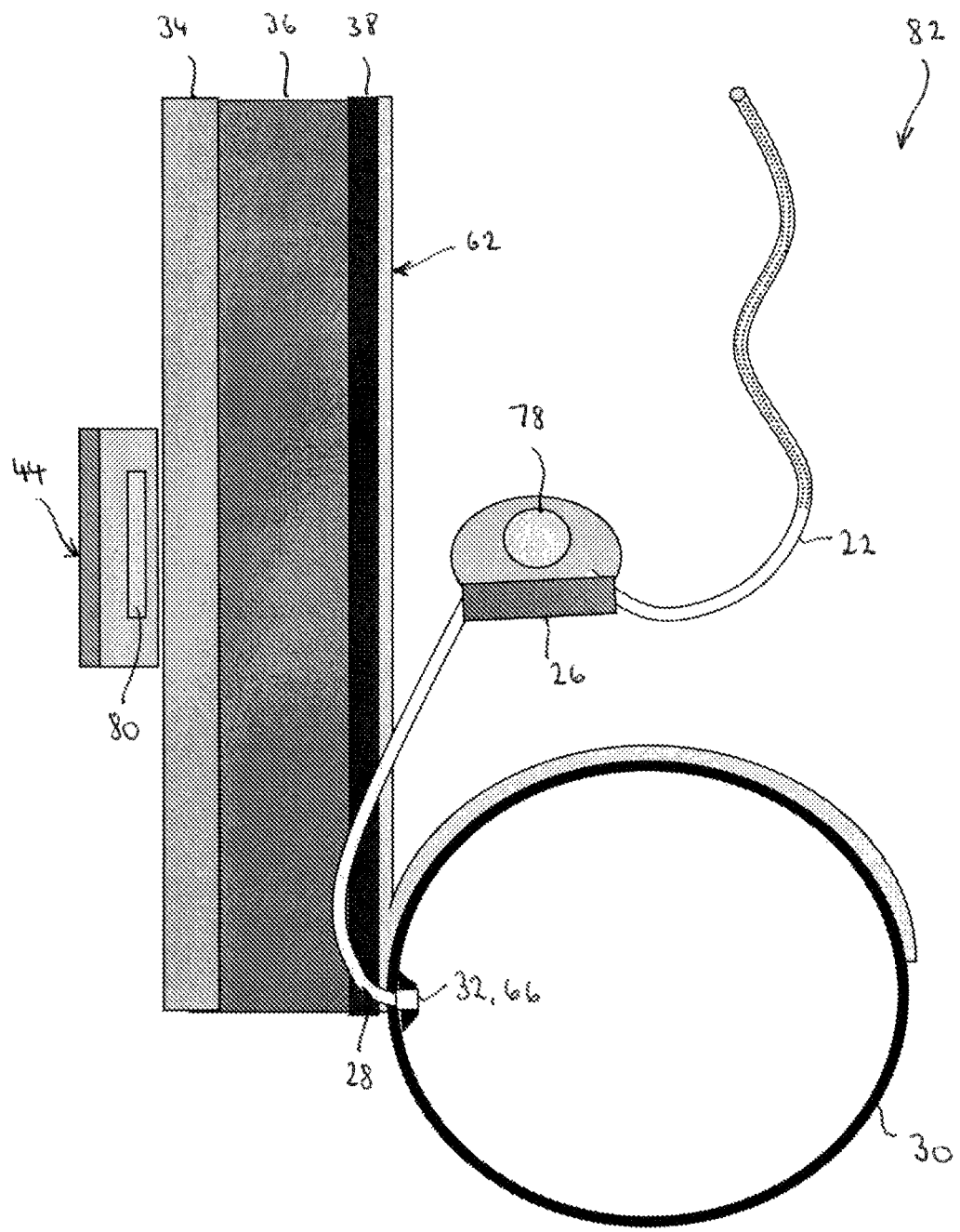
FIG. 7 illustrates an embodiment of the invention, in which the implanted pump is placed in a non-subcutaneous position.

FIGS. 6 and 7 illustrate an embodiment of the invention, in which a device 76 has a non-magnetically powered pump. The implanted pump is powered instead by a battery or other implantable power source and communicates with external interface 44 using radio-wave or electromagnetic signal generators and receivers 78, 80 to transfer information and/or activation signals. Pump 26 can be disposed subcutaneously or in any other region suitable for implantation (for example, in the peritoneal cavity as shown in FIG. 7) as long as it can communicate with control module 44. Pump 26 can also be internally through sensors 64 and 66. In this embodiment, it is desirable that the physician is able to intervene control module 44 and prevent the operation of pump 26 in undesirable circumstances. In one variant of the present embodiment, while sensors 64 and 66 exert negative feedback, the patient may still activate pump 26 using control module 44 at her discretion. This device can be easily programmed, for example, for daily drainage or to have no drainage when bladder 30 exceeds a certain pressure. Pump 26 may also be programmed to be actuated under certain circumstances, for example, when peritoneal pressure sensor 64 detects a pressure above a certain threshold.

Figure 8A:
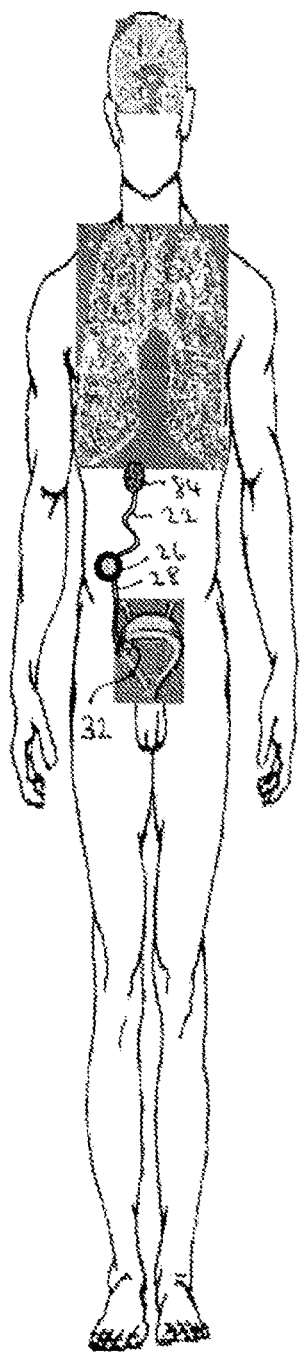
FIGS. 8A-8B illustrate some of the possible applications of a device according to the present invention.
Figure 8B:
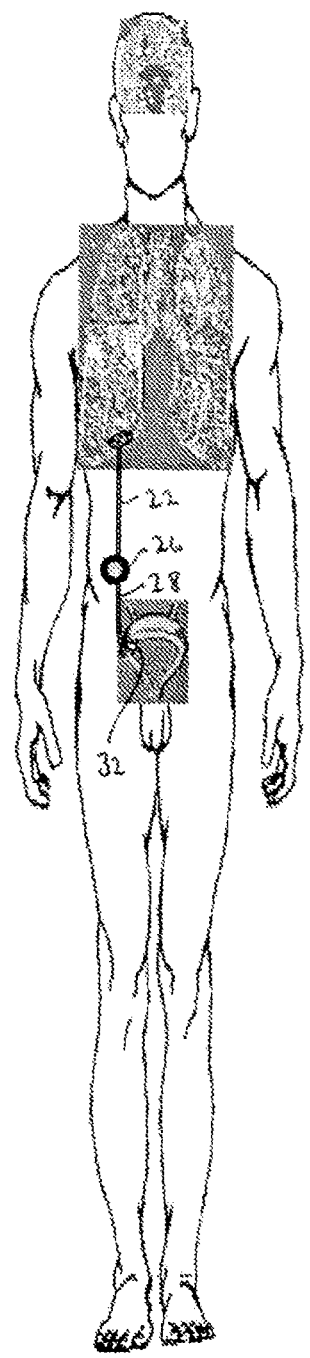

A device according to the present invention may collect fluids from different body cavities, for example, from the peritoneal cavity as shown in FIG. 8A, and from the pleural cavity as shown in FIG. 8B during the treatment of CHF. These figures show bladder anchor 32, outflow tube 28, pump 26, uptake tube 22, and the drainage ports for peritoneal 84 and pleural 86 drainage sites. It is important to note that any feature of the present invention can be employed in either of these applications.

Housing, shroud or casing of 40 of a device according to the present invention can take many shapes and the device can be manufactured from any of a variety of materials, the only requirement being biocompatibility. The device may also incorporate anti-infective components or coatings to prevent the spread of infection between body cavities. Such anti-infective components or coatings include, but are not limited to, bacteriostatic materials, bacteriocidal materials, one or more antibiotic dispensers, antibiotic eluting materials, entrained radioisotopes, a heating element, bioactive plastics, surfaces which encourage epithelialization, and coatings which prevent bacterial adhesion. Alternatively, a device according to the present invention may incorporate anti-clogging components or coatings, for example, active ultrasonic components, surfaces which encourage epithelialization, enzyme eluting materials, chemical eluting surfaces, and coatings which prevent adhesion of proteinaceous compounds.

The device of the present invention has been designed to allow for minimally invasive placement, and non-invasive radiographic imaging tools such as abdominal ultrasound may be employed during placement. By filling bladder 30 and using ultrasound to locate this space, outflow tube 28 can be placed through a small incision and a simple puncture. Uptake tube 22 can also be placed in a similar manner using subcutaneous tunneling of the tubing and ultrasound guidance. In one embodiment, once the tubing has been placed, uptake and outflow tubes 22 and 28 are attached to pump 26 at ports 54, 56, and 58 and pump 26 is disposed into its site of implantation (for example, into subcutaneous space 12) after which the wound is closed and allowed to heal.

The implantable fluid management device described hereinabove may include a fluid reservoir configured to protect a bodily region (for example, the pleural cavity) from being pumped dry, which may be undesirable in itself and which may cause that cavity to remain dry for an excessive amount of time.

Figure 9A:
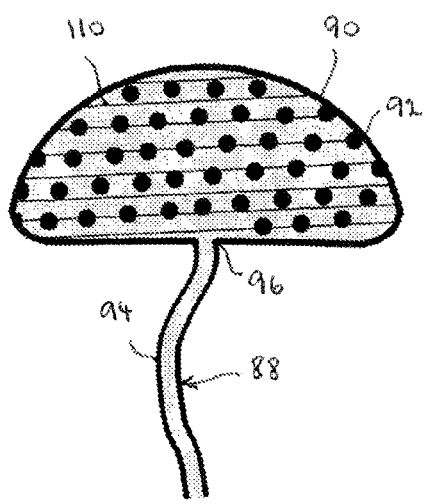
FIGS. 9A-9D illustrate an embodiment of an expanded reservoir catheter, in which a dome-shaped reservoir has perforations covering its surface.
Figure 9B:
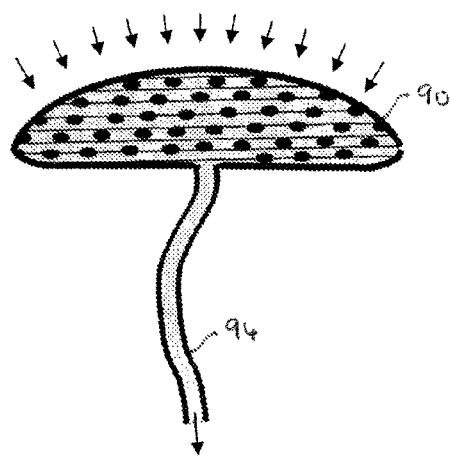
Figure 9C:
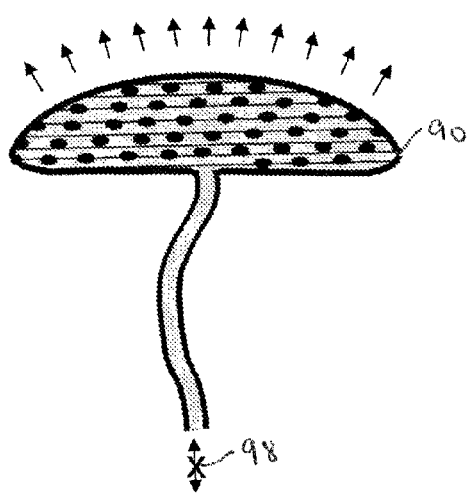
Figure 9D:
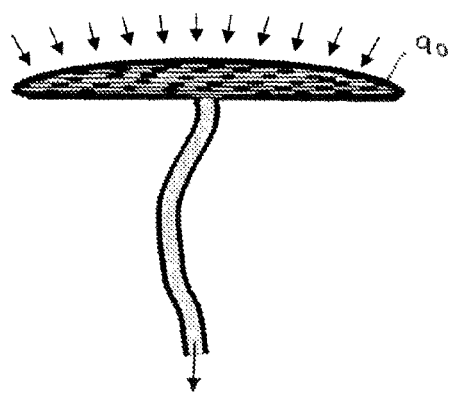

FIGS. 9A-9D illustrate an expanded reservoir catheter for use with an implantable fluid management device, which includes a reservoir 90 (seen in FIG. 9A), which is expandable by uptake of fluid and is collapsible (or contractible) by activation of pump 26, as shown in FIGS. 9B-9C. After contracting, reservoir 90 then expands gently until it has been filled, as seen in FIG. 9D, and pump 26 may then be reactivated to empty its contents again through catheter 94 (typically, the same tube as uptake tube 22). The activation of pump 26 may be triggered according to a set time table or by one or more of a variety of detectable parameters, including a spatial sensor to detect when reservoir 90 has expanded, a pressure sensor to detect expansion and collapse of reservoir 90, and an electrical detector capable of sensing the presence or absence of fluid and/or tissue in or around reservoir 90. The activation of pump 26 may also be triggered by an external signal, including a signal provided by a manually activated or an automated communication device such as a scale capable of detecting the weight of the patient and of activating or deactivating pump 26 based on the measured weight. By determining the weight of the patient, rapid changes can be interpreted as fluid weight gain and pump 26 may then be activated to remove fluid.

This embodiment of reservoir 90 is designed to be inserted in the body of the patient in a collapsed configuration and then pulled snug against the abdominal wall or other bodily cavity. This and other embodiments of the implantable fluid management device may also be coated, internally and externally, with a biocompatible coating such as a hydrophilic coating (which hinders crust formations), a polyethylene glycol based coating, an albumin coating, or another protein-based coating. In this and other embodiments of the device, reservoir 90 may be compressed by pressures of less than 10 mmHg, less than 20 mmHg, less than 50 mmHg, less than 100 mmHg or less than 200 mmHg. By minimizing the vacuum required to compress reservoir 90, the vacuum transmitted to abdominal wall 14 or to surrounding tissues is kept to the safest, lowest level.

Reservoir 90 may include a support structure 110, for example, a support structure manufactured from Nitinol (a nickel-titanium alloy) or other shape-memory material, and has perforations 92 disposed on at least a portion of its outer surface to allow the target fluid to enter and fill reservoir 90. Support structure 110 not only provides for a homogeneous expansion and contraction of reservoir 90 and for uniform pressure of reservoir 90 against the body cavity, where reservoir 90 is disposed, but in one embodiment may also provide for a recoil action that facilitates return of reservoir 90 to the expanded configuration after contracting. This recoil action creates a suction towards and into reservoir 90 and, consequently, promotes removal of undesired liquid from the body cavity, In the illustrated embodiment, reservoir 90 has a hemispherical shape, which generally includes a dome-shaped portion and an essentially flat portion. A drainage port 96 may be position in a variety of locations, for example, in the central part of the essentially flat portion as shown in FIGS. 9A-9D, and a valve 98 for preventing backflow from pump 26 into reservoir 90 may also be included. Alternatively or in addition to valve 98, backflow may be prevented by utilizing a unidirectional pump.

Figure 10A:
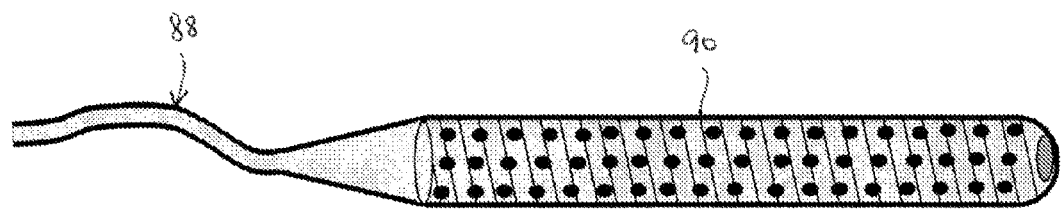
FIGS. 10A-10C illustrate a different embodiment of an expanded reservoir catheter, in which the reservoir has perforations covering its surface.
Figure 10B:
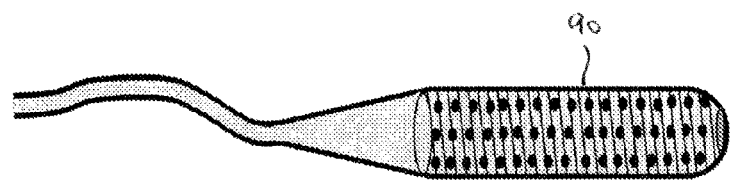
Figure 10C:
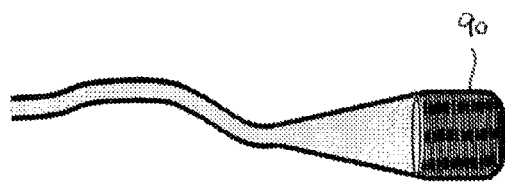
Figure 11A:
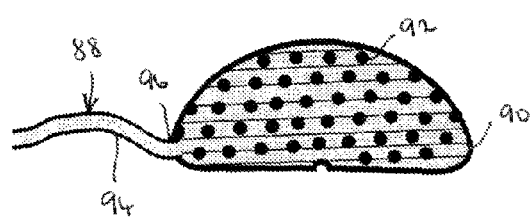
FIGS. 11A-11D illustrate another embodiment of an expanded reservoir catheter, in which a dome-shaped reservoir has perforations covering its surface.
Figure 11B:
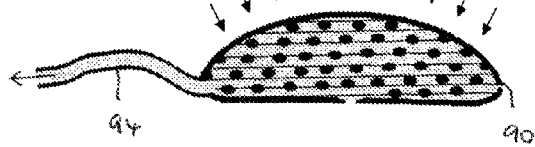
Figure 11D:
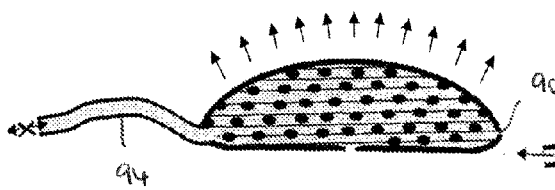
Figure 11C:
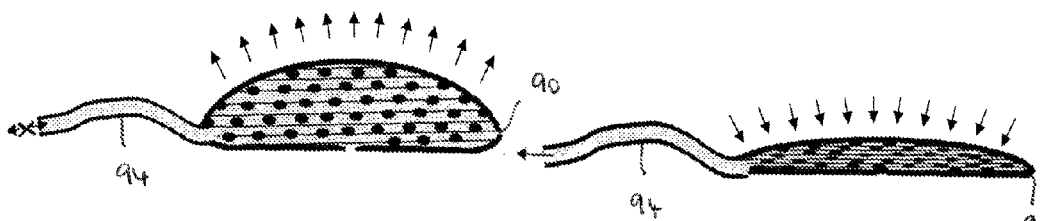

FIGS. 10A-10C illustrate an expanded tubular reservoir catheter 88 that includes reservoir 90, which is contracted by activation of pump 26. In the present embodiment, reservoir 90 has a generally cylindrical shape that can compress or expand along its longitudinal axis. As with the hemispherical embodiment depicted in FIGS. 9A-9D, after contracting reservoir 90 then expands gently until it has becomes filled again and pump 26 may then be reactivated to empty its contents again. The activation of pump 26 may be triggered according to a set time table or by one or more of a variety of detectable parameters, including a spatial sensor to detect when the reservoir has expanded, a pressure sensor to detect expansion and collapse of the reservoir, and an electrical detector capable of sensing the presence or absence of fluid and/or tissue in or around the reservoir. The activation of pump 26 may also be triggered by external signals, including a manually activated communication device or an automated communication device such as a scale capable of detecting the patient's weight and activating or deactivating the pump based on the weight of the patient. By determining the weight of the patient, rapid changes can be interpreted as fluid weight gain and pump 26 may be activated to remove fluid. This embodiment of reservoir 90 is designed to be inserted into the target bodily cavity and may include a weight at the tip of catheter 88, to ensure that it reservoir 90 is held in the most dependent portion of the cavity to be drained.

FIGS. 11A-11D illustrate an embodiment of the invention similar to that of FIG. 9, except that drainage port 96 is situated in the proximity of an edge of reservoir 90, where the dome portion of reservoir 90 meets the essentially flat portion of reservoir 90, as depicted in FIGS. 11A-11D. Perforations 92 are typically disposed over the entire outer surface of reservoir 90, but in different variants of this embodiment, perforations 92 may be disposed only within selected areas of reservoir 90. A weight at the tip of the catheter 94 may also be included to ensure that reservoir 90 is held in the most dependent portion of the cavity to be drained.

Figure 12A:
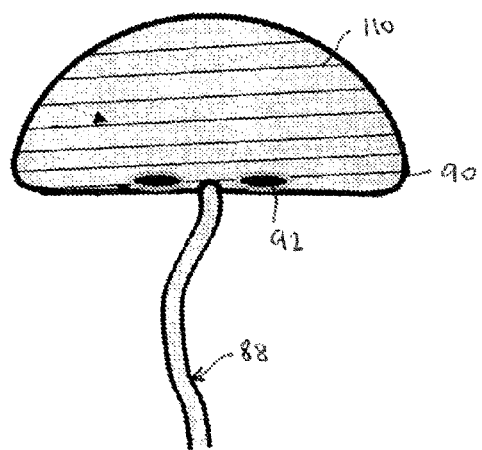
FIGS. 12A-12B illustrate an embodiment of the invention, in which the reservoir includes perforations in recessed positions.
Figure 12B:
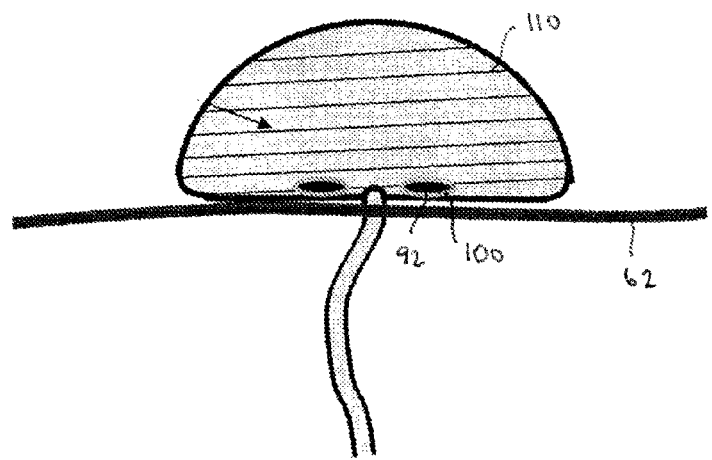

FIGS. 12A-12B illustrate another embodiment if reservoir catheter 88, in which reservoir 90 is collapsible from an expanded configuration (FIG. 12A) to a collapsed configuration (FIG. 12B) by activation of pump 26. After contracting due to the negative pressure provided of pump 26, reservoir 90 may then expand back gently until it has been filled again, after which pump 90 may be activated again to empty the contents of reservoir 90. The activation of pump 26 may be triggered according to a set time table or by one or more of a variety of detectable parameters, including a spatial sensor detecting when reservoir 90 has expanded, a pressure sensor to detect expansion and collapse of reservoir 90, and an electrical detector sensing the presence or absence of fluid and/or tissue in or around reservoir 90. The activation of pump 26 may also be triggered by external signals, including a manually activated communication device or an automated communication device such as a scale capable of detecting the patient's weight and of activating or deactivating pump 26 based on the weight of the patient. By determining the weight of the patient, rapid changes can be interpreted as fluid weight gain and pump 26 may be activated to remove fluid.

The embodiment of FIGS. 12A-12B is configured to have reservoir 90 inserted into the patient's body in a collapsed configuration and then pulled snug up against abdominal wall 62 or other bodily cavity. Reservoir 90 may utilize perforations 92 only in regions of reservoir 90 that will have no contact with the surrounding bowel and/or tissues. By pulling the device snug up against abdominal wall 62, channels or flutes 100 may be used to ensure that the surrounding bowel/tissues do not occlude perforations 92, to which the channels or flutes 100 lead, while also preventing abdominal wall 62 from obstructing channels or flutes 100. Reservoir 90 may also be supported by a support structure 110, which may be manufactured from a variety of biocompatible materials, for example, from a Nitinol shape-memory material and which may provide additional during expansion of reservoir 90, as described previously.

Figure 13:
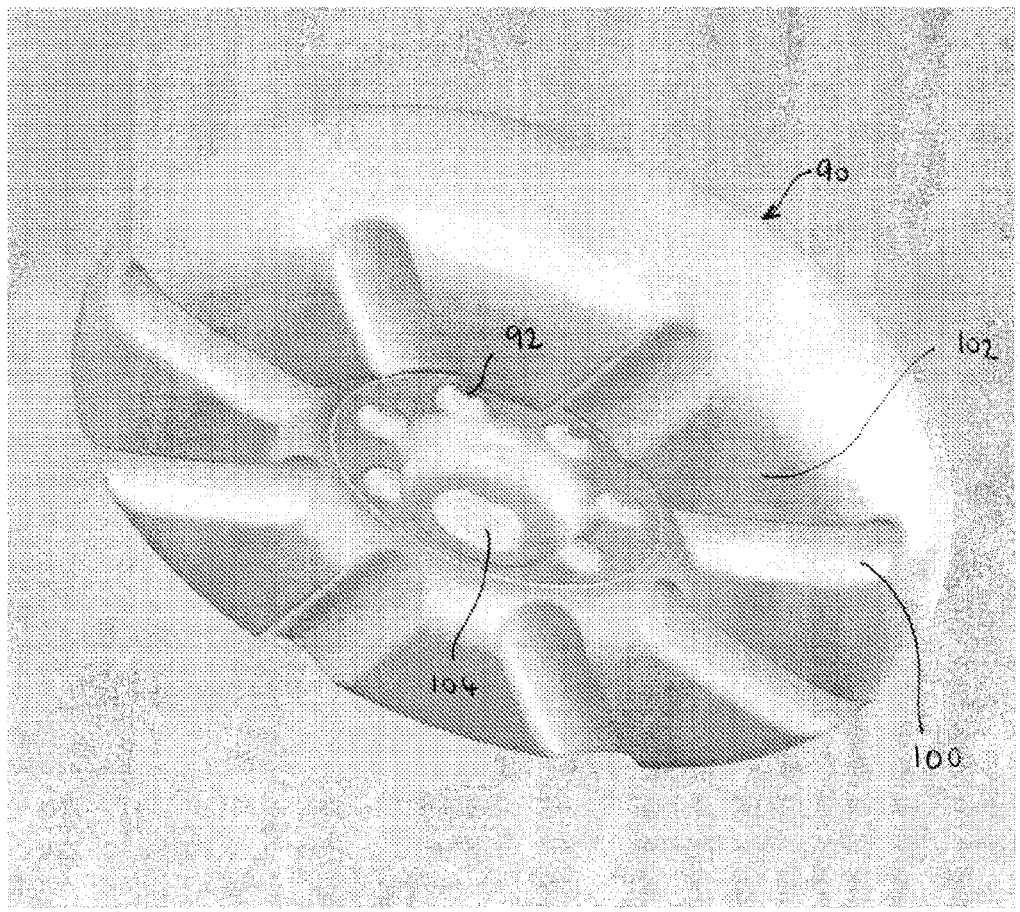
FIG. 13 illustrates a perspective view of the underside of the reservoir according to one embodiment of the invention.

Some features of the embodiment depicted in FIGS. 12A-12B will now be described with reference to FIG. 13. More particularly, FIG. 13 is a perspective view of the underside of the device shown in FIGS. 12A-12B, which typically contacts abdominal wall 62 and which includes channels or flutes 100. Such channels or flutes 100 promote flow of fluid towards protected perforations 92, held against abdominal wall 62, without allowing omentum or mesentery to come into contact with perforations 92. The regions 102 between channels or flutes 100 and/or exit tubing 104 leading from reservoir 90 may be coated with materials such as Dacron or ePTFE, or with a porous material that encourages tissue ingrowth, thereby firmly anchoring reservoir 90 in place against abdominal wall 62, or against a wall of the cavity into which the reservoir 90 is implanted. With this configuration, the bowel and other tissues surrounding the device may be less likely to track between the device and abdominal wall 62 while the fluid may still readily track through the specifically designed protective channels or flutes 100.

Figure 14:
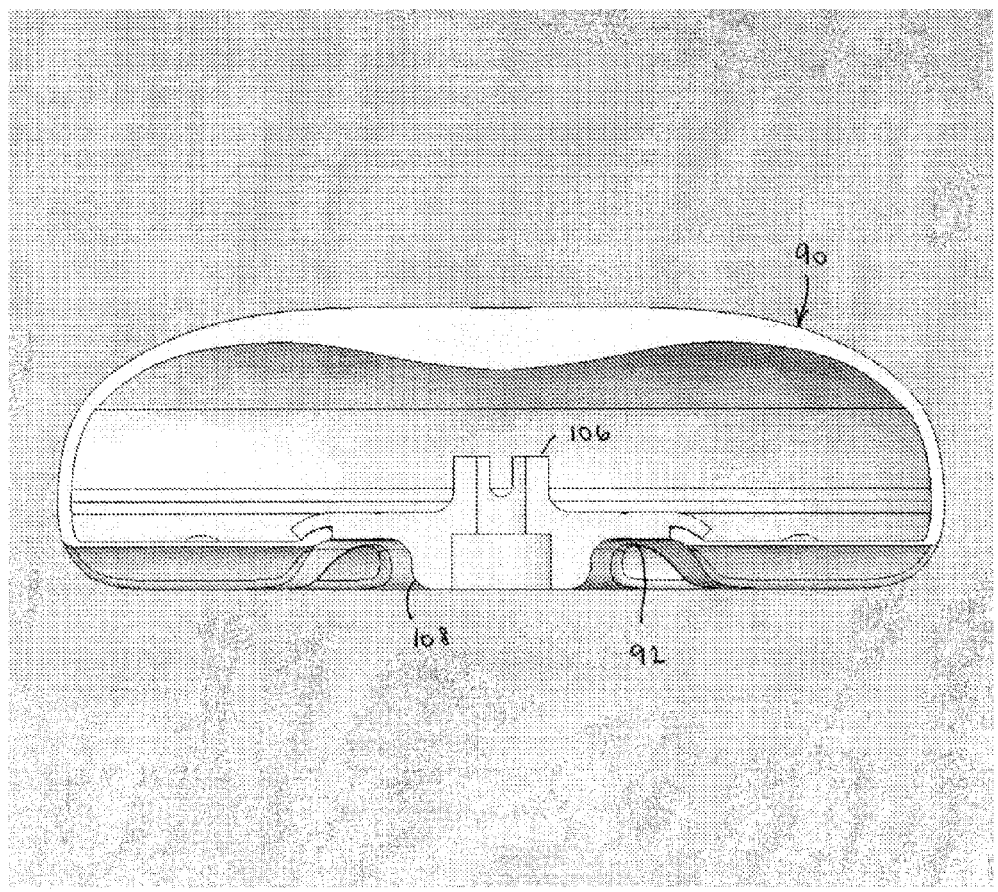
FIG. 14 illustrates a cross-section of the reservoir of FIG. 13, further comprising a dehydration prevention element.
Figure 15A:
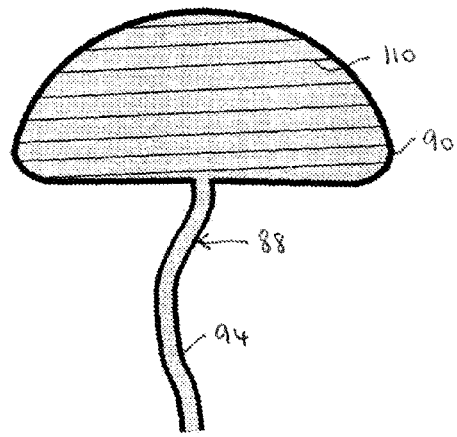
FIGS. 15A-15D illustrate different operative positions of a dome reservoir having semi-permeable micro-perforations.
Figure 15B:
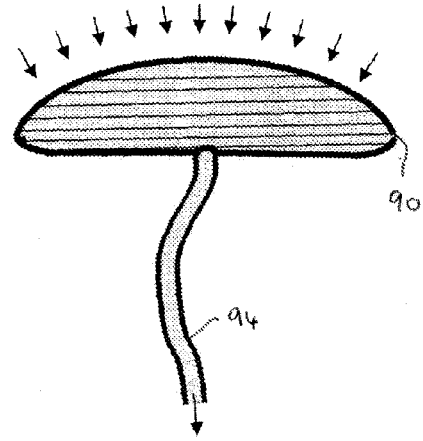
Figure 15D:
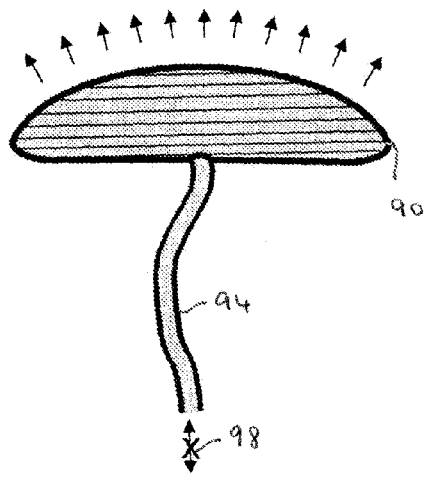
Figure 15C:
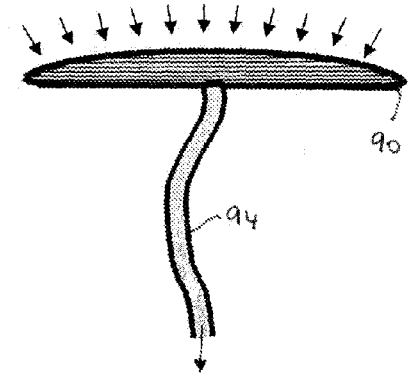

FIG. 14 illustrates a cross-section of reservoir 90, more particularly, of a dehydration prevention feature included in this embodiment. In this embodiment, the presence of dehydration prevention element 106 causes pump 26 or other sensor 48 coupled to pump 26 to detect when the reservoir becomes compressed. If reservoir 90 is still in a collapsed state at the next activation of pump 26, pumping may be cancelled to prevent dehydration of the bodily cavity, because the bodily cavity may have become too dry to adequately refill reservoir 90. Dehydration element 196 also prevents excessive vacuum from being applied to the wall of the cavity to be drained, beyond the negative feedbacks provided to pump 90, so that flow and application of vacuum are triggered only after a certain threshold is reached.

FIG. 14 also illustrates over-insertion prevention support structure 108, configured to pull the device up against abdominal wall 62 without forcing recessed perforations 92 be positioned too tightly against wall 62.

FIGS. 15A-15D illustrate an embodiment of reservoir 90 having a dome-shaped configuration and also having semi-permeable micro-perforations (not shown). Those semi-permeable perforations may be employed in reservoirs of different shapes and configuration beyond the specific shape of the reservoir depicted in FIGS. 15A-15D and may replace the larger, full drainage perforations on least a portion of the surface of reservoir 90, in order to selectively retain and remove components from the fluid being drained. Semi-permeable micro-perforations may be introduced on reservoir 90 by a coating process or through material selection. The collapse and possible recoil of reservoir 90 operates like in the other embodiments described herein, with the negative pressure caused by the optional recoil feature causing flow in reservoir 90 only of compounds that are capable of passing the semi-permeable barrier. After vacuum is applied to the outlet of reservoir 90, or reservoir 90 itself is subjected to positive pressure (that is, to compression), reservoir 90 collapses and empties of the fluid therein into catheter 94, after which compliance of reservoir 90 once again encourages fluid influx.

As previously discussed, fluid ingressions into reservoir 90 may be further encouraged by the recoil action of support structure 110, which may be made of Nitinol among different possible materials, and this fluid removal process may be repeated as long as necessary to remove and/or retain compounds of interest from the target body cavity. The recoil of shape-memory structure 110 allows for a repeated, consistent force to induce selective permeation while creating a duty cycle usable in any potentially implantable device due to the short bursts of reservoir emptying. These bursts are able to effectively drain fluid, which would otherwise not have been safely drained from the surrounding tissues, if, for example, tissue would be rapidly pulled into the perforations.

Figure 16B:
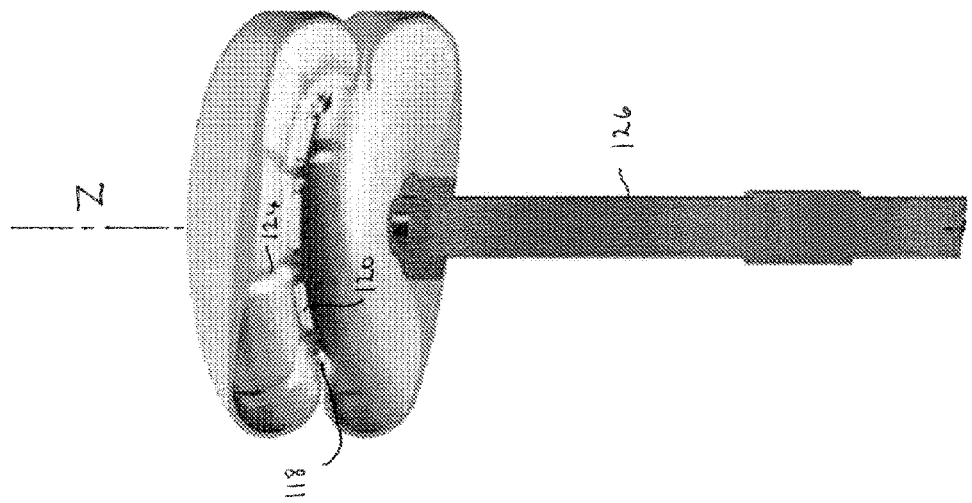
FIGS. 16A-16B illustrate an embodiment an expanded reservoir catheter having a reservoir defined by an upper element and a lower element and an annular surface therebetween, more particularly, a perspective view (FIG. 16A) and a cross-sectional view (FIG. 16B) of such embodiment.
Figure 16A:
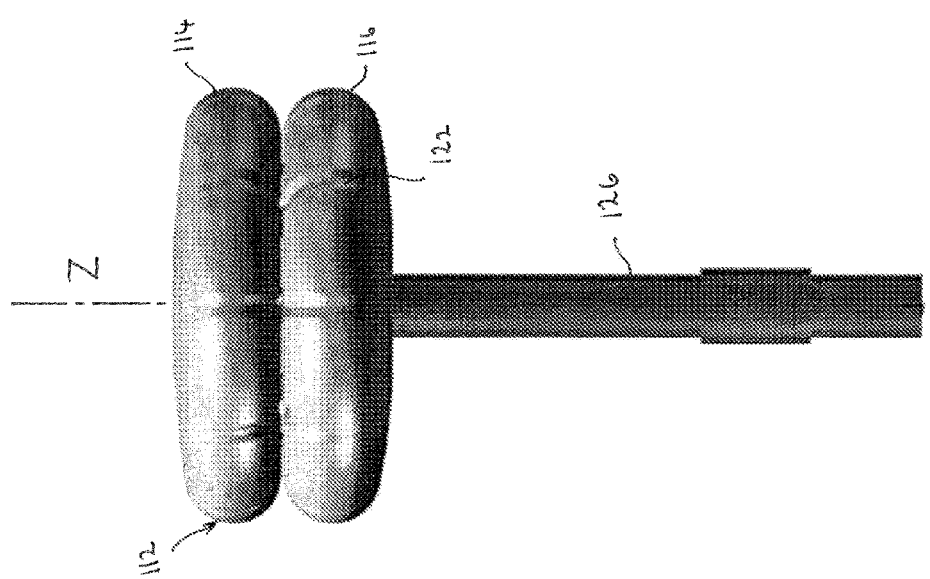

FIGS. 16A-16B illustrate one more embodiment of a reservoir system for draining excess fluid from a body cavity. Referring first to FIG. 16A, a reservoir 112 includes an upper reservoir element 114 and a lower reservoir element 116, which in the depicted embodiment are each shaped like a disk expandable longitudinally along its shorter axis, labeled in FIGS. 16A-16B as axis Z. A person skilled in the art will appreciate that, in different variants of the present embodiment, more than two reservoir elements may be included and that the reservoir elements may have different shapes and expand along different axes.

The cross-section view of FIG. 16B shows that upper reservoir element 114 and lower reservoir element 116 are adjoined along an annular surface 118, which extends along the junction area between upper reservoir 114 and lower reservoir 116 to form a groove, and which contains one or more annular openings or inlets 120, shaped as slots cut along annular surface 118 Annular inlets 120 enable the ingression of the fluid to be drained into reservoir 112, which, in a manner similar to previously described embodiments, is configured to expand and contract longitudinally along axis Z. One of the benefits provided by this embodiment is the prevention of contact between inlets 120 and a wall of the body cavity, within which reservoir 112 is disposed.

Each of reservoir elements 114 and 116 may have grooves or flutes 122 carved radially along their outer surfaces and defined by depressions which conversely define ribs 124 extending radially along their inner surfaces. One skilled in the art will appreciate that grooves or flutes 122 promote flow of fluid towards annular surface 118 and inlets 120, while at the same time ribs 124 (formed by the depressions of grooves or flutes 122) operate as internal stiffeners along annular surface 118, enabling reservoir 112 to maintain its basic configuration in spite of the weakening of annular surface 118 caused by annular inlets 120 and to expand and contract along axis Z in a bellows-like fashion.

In the illustrated embodiment, inlet 120 are disposed symmetrically between pairs of grooves or flutes 122, while ribs 124 extend uninterrupted from reservoir element 114 to reservoir element 116. A person skilled in the art will appreciate that different arrangements of groves or flutes 122 and, conversely, of ribs 124 are possible, as well as of inlets 120, and that all such alternative arrangements fall within the scope of the present invention.

Catheter 126 is fluidly coupled to reservoir 112, so to carry away the liquid contained in reservoir 112, particularly upon the action of pump 26 (not shown). While catheter 126 is shown as coupled to reservoir 112 in a central position within its lower surface, a person skilled in the art will appreciate that catheter 126 may be fluidly coupled to reservoir 112 at different other locations, for example, at a lateral site in a manner similar to the embodiment shown in FIGS. 11A-11D. In addition, each of reservoir elements 114 and 116 mat have a variety of shapes, for example, may have cylindrical shapes like the embodiment depicted in FIG. 10 and may also be connected one to the other at a variety of locations.

While the device is primarily contemplated for use in human patients, it is contemplated that the invention will have veterinary applications in other mammalian species, for example, in equine, bovine, canine, and feline species.

The present invention has been described herein in connection with the above described embodiments, but it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. An implantable fluid management device comprising:
    an implantable pump;
    a reservoir;
    an uptake tube having a proximal end in fluid communication with the reservoir and a distal end in fluid communication with the pump; and
    an outflow tube having a proximal end in fluid communication with the pump and a distal end configured for fluid communication with a patient's bladder,
    wherein actuation of the pump is triggered by a sensor in fluid communication with at least one of the reservoir and a peritoneal cavity, the sensor directly monitoring pressure to prevent excessive vacuum from being applied to the peritoneal cavity.

2. The implantable fluid management device of claim 1, wherein the reservoir is configured for implantation in the peritoneal cavity.

3. The implantable fluid management device of claim 1, wherein the reservoir is configured to expand and to contract.

4. The implantable fluid management device of claim 1, wherein the reservoir is coupled to a port.

5. The implantable fluid management device of claim 1, wherein the reservoir is configured to expand upon ingress of fluid into the reservoir.

6. The implantable fluid management device of claim 1, wherein the sensor is further configured to monitor flow.

7. The implantable fluid management device of claim 1, further comprising another sensor configured to monitor pressure, flow, parameters of interest, or a combination thereof.

8. The implantable fluid management device of claim 1, wherein the reservoir comprises an outer surface having perforations disposed on at least a portion of the outer surface, the perforation providing for the ingression of the fluid from the peritoneal cavity into the reservoir.

9. The implantable fluid management device of claim 8, wherein at least some of the perforations are disposed in a recessed position in relation to the outer surface.

10. The implantable fluid management device of claim 8, further comprising a plurality of recesses disposed on at least a portion of the outer surface of the reservoir, the recesses promoting flow of the fluid from the peritoneal cavity towards at least some of the perforations.

11. The implantable fluid management device of claim 8, wherein the perforations are configured to prevent ingression into the reservoir of predetermined components of the fluid.

12. The implantable fluid management device of claim 1, wherein the reservoir includes a support structure.

13. The implantable fluid management device of claim 12, wherein the support structure provides for a recoil of the reservoir after contracting, the recoil promoting an expansion of the reservoir after the removal of the fluid.

14. The implantable fluid management device of claim 1, further comprising means for preventing backflow from the outflow tube to the uptake tube.

15. The implantable fluid management device of claim 1, wherein the reservoir comprises a dehydration prevention element preventing actuation of the pump when the reservoir is in a contracted condition.

16. The implantable fluid management device of claim 1, further comprising a weight configured to cause the reservoir to be disposed in a desired position after implantation of the device.

17. The implantable fluid management device of claim 1, wherein actuation of the pump may be triggered or terminated by a device external to the patient's body and configured to communicate wirelessly with the pump.

18. A method for transferring fluid, the method comprising:
    implanting a pump within a patient;
    implanting an uptake tube having a proximal end in fluid communication with a reservoir and a distal end in fluid communication with the pump;
    implanting an outflow tube having a proximal end in fluid communication with the pump and a distal end configured for fluid communication with the patient's bladder;
    triggering actuation of the pump by a sensor in fluid communication with at least one of the reservoir and a peritoneal cavity; and
    directly monitoring pressure to prevent excessive vacuum from being applied to the peritoneal cavity.

19. The method of claim 18, further comprising implanting the reservoir in the peritoneal cavity.

20. The method of claim 18, further comprising pumping fluid into the reservoir using the pump to expand the reservoir.

* * * * *